United States Patent
Warren

(10) Patent No.: US 6,302,559 B1
(45) Date of Patent: Oct. 16, 2001

(54) ELECTROLUMINESCENT NIGHT LIGHT AND AIR FRESHENER UNIT

(75) Inventor: William D. Warren, Shaker Heights, OH (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/447,851

(22) Filed: Nov. 23, 1999

(51) Int. Cl.⁷ .................................................. F21V 23/00
(52) U.S. Cl. ................ 362/226; 362/96; 362/92; 362/253; 362/84
(58) Field of Search ................ 362/96, 92, 253, 362/84

(56) References Cited

U.S. PATENT DOCUMENTS

| | | |
|---|---|---|
| D. 331,292 | 11/1992 | Ham . |
| D. 332,488 | 1/1993 | Martin . |
| D. 332,836 | 1/1993 | Ham . |
| D. 342,799 | 12/1993 | Ham . |
| D. 350,209 | 8/1994 | Martin . |
| 5,465,198 * | 11/1995 | Kellogg ................................ 362/253 |
| 5,556,192 * | 9/1996 | Wang ................................... 362/276 |
| 5,779,346 * | 7/1998 | Burke ..................................... 362/84 |
| 5,796,914 | 8/1998 | Gatzenmeyer et al. . |
| 6,099,137 * | 8/2000 | McCormack et al. ............... 362/96 |
| 6,190,017 * | 2/2001 | Lei ......................................... 362/84 |

OTHER PUBLICATIONS

Renuzit® (The Drackett Company, Cincinnati, Ohio), Model No. KL0003, Dual Comp. Air Freshener, 120 V. 2.0 watts, 60 Hz.

\* cited by examiner

Primary Examiner—Stephen Husar
Assistant Examiner—Anabel Ton
(74) Attorney, Agent, or Firm—Fay, Sharpe, Fagan, Minnich & McKee, LLP

(57) ABSTRACT

A combined electroluminescent plug-in night light incorporates an air freshener in a single unit. The unit plugs into a standard wall outlet and provides a continuous, low wattage light source and the desired air freshening. It includes a low operating temperature, is highly energy efficient, and the compact, space saving design are desirable features.

7 Claims, 1 Drawing Sheet

ELECTROLUMINESCENT NIGHT LIGHT AND AIR FRESHENER UNIT

BACKGROUND OF THE INVENTION

1. Field of the Invention

This application relates to low wattage night lights and electrically activated air fresheners, and particularly to an integrally combined electroluminescent night light and air freshener unit.

2. Discussion of the Art

It is known in the art to provide a room air freshener unit that is electrically actuated, i.e., designed to be plugged into a wall outlet to power a small heating element. The heating element surrounds a cavity or receptacle in which a thermally activated or diffused substance is stored. The thermally diffused substance is typically a refillable packet or replaceable cartridge that is activated by the heat. A series of openings are provided in the housing to radiate the diffused substance to the room. Over time, a new supply of air freshener substance is required. Thus easy access is provided to the housing container to remove the used container and insert a new one.

Today's home has found a substantial increase in the number of electrical appliances and devices. Not surprisingly, market studies indicate an increased demand for electric outlets throughout the house. One particular example of the scarcity of outlets is in bathrooms where there are a number of demands for the outlets in association with a wide variety of uses. For example, hair dryers, styling irons, electric shavers, electric toothbrushes, etc. are all examples of AC powered products that are prevalent in the bathroom. In additional, consumers often maintain a night light in the bathroom.

Incandescent night lights are the most widely used type of night light. However, more recent development has focused on the development of electroluminescent lamps (EL lamps). Rather than using an incandescent coil as the light source, EL lamps convert electrical energy into light by applying an electric field across a thin phosphor layer to produce or emit light. A phosphor layer is interposed between first and second conductive electrodes. One of the electrodes is light transmissive, or optically clear. The AC voltage across the electrodes causes the phosphors to emit light during each cycle. By controlling the voltage and the frequency, the light brightness will alter, and also to some degree the color.

These types of electroluminescent light sources have found widespread use as night lights because of the level of lamp brightness that is generally unaffected by voltage, frequency, temperature, etc. The lights also do not fail in an abrupt manner. For example, incandescent light sources fail abruptly upon failure of the coil. Electroluminescent lamps, on the other hand, generally undergo a gradual decrease in brightness over time and are generally rated with extended useful lives relative to incandescent night lights. Thus, EL night lights are generally considered low maintenance since they do not require replacement as encountered, for example, with incandescent night lights. Moreover, EL night lights are very efficient and may only consume current on the level of milli-amps as to draw power at, for example, approximately 0.3 watts. They are also very cool operating lamps, as opposed to the heat generated by an incandescent lamp. Thus, the absence of heat generation plays an important factor for reasons to be noted.

Also related to the number of outlets is the fact that known separate air freshener and night light units cannot be accommodated in the same dual outlet wall socket because of the extended profiles of the air freshener and night light structures. The extended profiles dictate whether the unit is oriented in a particular manner in the outlet to provide access to the other outlet in a dual outlet arrangement.

Thus, a need exists to provide these desired functions without contributing to the problems noted above in a simple, effective manner.

BRIEF SUMMARY OF THE INVENTION

In an exemplary embodiment of the invention, a combined night light and air freshener unit includes a storage compartment adapted to receive an air freshener cartridge therein. A heating element is disposed adjacent the storage compartment and powered via a male plug adapted for receipt in a conventional electrical socket. In addition, a low wattage electroluminescent lamp integrally extends from the storage compartment and is powered via the same plug.

The exemplary embodiment conforms the width of the nightlight to that of the storage compartment to minimize the dimensions of the overall unit.

The exemplary embodiment preferable integrally molds the electroluminescent night light and air freshener in the same housing to minimize assembly steps and overall dimensions of the unit.

DETAILED DESCRIPTION OF THE INVENTION

Figure 1:
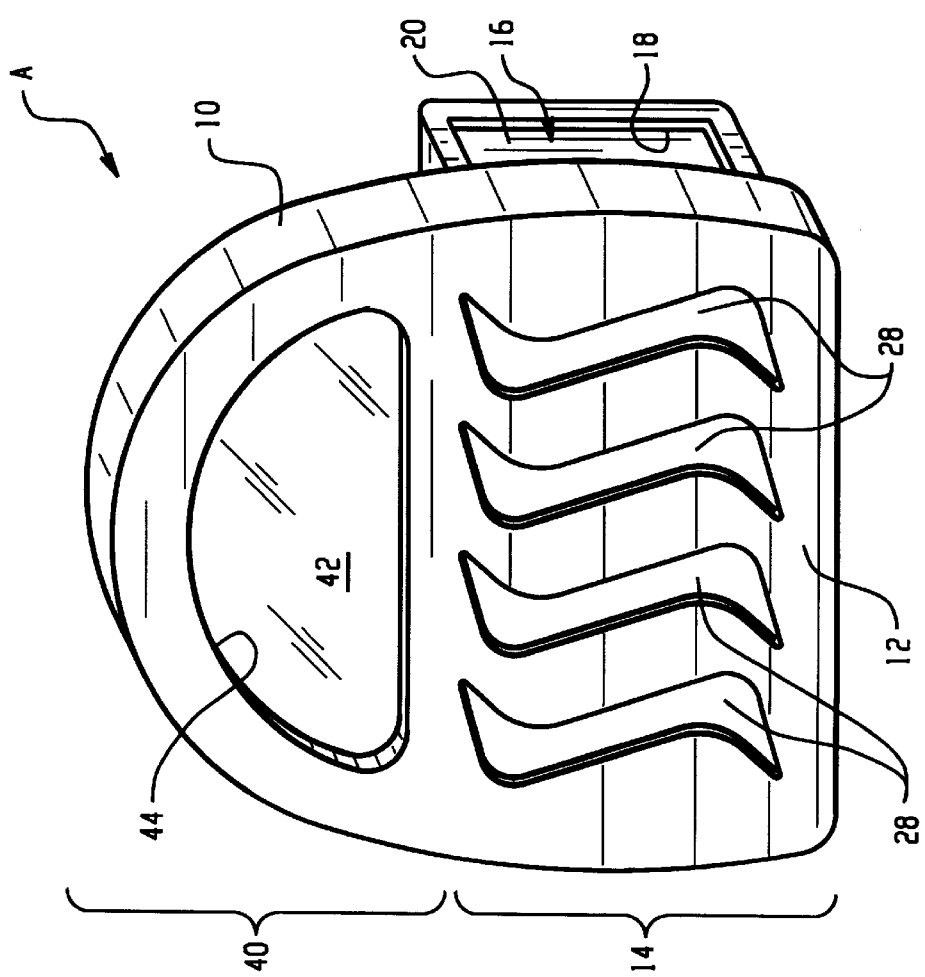
FIG. 1 is a perspective view of the present invention.

A combined electroluminescent nightlight and air freshener unit A is shown in FIG. 1. It includes an integrally molded housing 10, such as a plastic housing, that has a generally planar front or first face 12. A first or lower portion 14 of the housing comprises the air freshener housing. It includes a storage compartment 16 having an opening 18 providing ease of access to the storage compartment. The storage compartment is dimensioned and adapted to receive a refillable packet or replaceable cartridge of a thermally diffused substance 20. The storage compartment extends from a second or rear face 22 of the housing and a male plug 24 protrudes outwardly therefrom to provide electrical connection with an electrical socket or wall outlet (not shown). Although the individual blades of the male plug are oriented in a vertical direction, it will be appreciated that the blades can be oriented at other angles as desired. The plug is electrically connected to a heater element 26 associated with the air freshener portion of the unit. The heater element is represented in dashed line and it will be understood that the heater element is a resistive element that heats the storage compartment in a manner well known in the art. Examples of known arrangements are shown and described in, for example, published PCT application WO 98/11924, D 350, 209, and D 332,488, as well as the associated commercial products which are well known in the art.

A series of fragrance dispensing openings 28 are preferably provided in the front face 12 of the device. Stylized openings are illustrated, although it will be recognized that various opening configurations may be adopted without departing from the scope and intent of the present invention. Typically, the openings are directed outwardly toward the room and thus are oftentimes preferably disposed in the opposite face of the unit from the plug.

A second portion 40 of the unit comprises an electroluminescent night light. It is also electrically connected to the male plug 26. The EL night light includes a visible light transmissive panel 42 which, as described in the background, is typically one of the electrodes that form the well known electroluminescent lamps. The housing 10 includes an enlarged opening 44 in the planar face 12 to maximize the amount of light that is emitted from the light panel 42. As shown in FIG. 1, the opening is semicircular in conformation although it will be understood that the opening or night light configuration may be altered without departing from the scope and intent of the invention. The embodiment of FIG. 1 illustrates that the overall width of the integral unit is preferably not increased by incorporating the EL night light and air freshener portions into a single unit. It is also preferred that the housing is an integrally molded arrangement for ease of assembly. Thus, the planar face 12 is a mere extension of the air freshener portion and easily accommodates the EL night light portion. It preferably extends in a longitudinal direction away from the air freshener portion. Of course, the EL night light could also be disposed on different faces of the unit without departing from the present invention.

Figure 2:
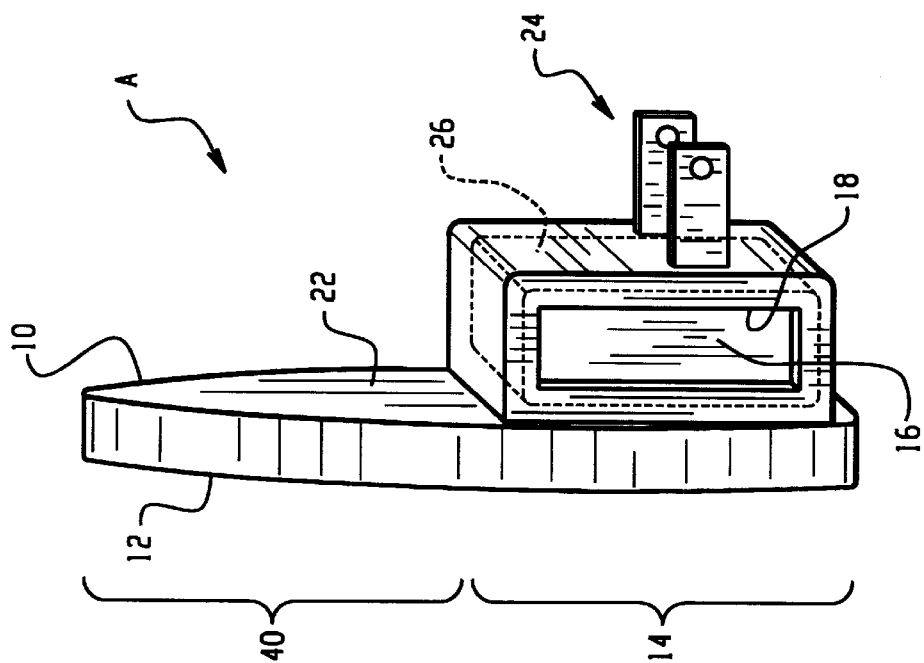
FIG. 2 is an elevational view taken generally from the right-hand side of FIG. 1.

As best illustrated in FIG. 2, since the EL night light is a thin panel assembly, it does not adversely impact on receipt of the wall plug 24 into an outlet. Thus, the overall depth of the unit is not increased or adversely affected. This minimizes the number of outlets required for different functions in the wall outlet. It also exhibits a low profile structure and the cool temperature of the night light does not adversely impact on the desired heat level for the refillable air freshener cartridge. As will be appreciated, too much heat would quickly dispense or thermally diffuse the volatile component of the air freshener and result in frequently refilling or replacement of the cartridges.

The invention has been described with reference to the preferred embodiment. Obviously, modifications and alterations will occur to others. The invention is intended to cover such modifications and alterations insofar as they fall within the scope of the appended claims or the equivalents thereof.

What is claimed is:

1. A combination night light and air freshener unit comprising:

a storage compartment dimensioned to receive an associated air freshener cartridge therein, at least one wall of the storage compartment having openings therein to allow vaporized air freshener to escape to ambient;

at least one wall of the storage compartment including a heating element for raising the temperature of an associated air freshener cartridge in response to enersization of the heating element;

a male plug extending from the storage compartment for receipt in a n associated electrical outlet;

a low wattage electroluminescent night light integrally extending from the storage compartment; and said low wattage electroluminescent night light producing a cool operating temperature so as not to increase thermal diffusion of a volatile component of the air freshener cartridge.

2. The combination night light and air freshener unit of claim 1 wherein the nightlight is electrically connected to the male plug.

3. The combination night light and air freshener unit of claim 1 wherein the nightlight has a width that is substantially identical to the storage compartment.

4. The combination night light and air freshener unit of claim 1 wherein the storage compartment includes an enlarged access in a sidewall thereof that receives an associated air freshener cartridge therein.

5. The combination night light and air freshener unit of claim 1 wherein the night light is an electroluminescent light source having a phosphor layer interposed between first and second electrodes.

6. The combination night light and air freshener unit of claim 1 wherein the night light is coplanar with the wall of the storage compartment having the openings therein.

7. An integral low wattage night light and heated air freshener unit comprising:

a storage compartment dimensioned to receive an air freshener cartridge therein, a front wall of the storage compartment having spaced openings therein that allow vapors from the heated air freshener cartridge to escape the storage compartment to ambient;

a heating element molded into the walls of the storage compartment for raising the temperature of the air freshener cartridge in response to energization of the heating element;

a low wattage electroluminescent night light including a phosphor layer interposed between first and second electrodes integrally extending from the storage compartment;

said low wattage electroluminescent night light producing a cool operating temperature to thereby prevent a volatile component of the air freshener cartridge from being dispensed rapidly; and a male plug extending from the storage compartment for receipt in an associated electrical outlet, the male plug electrically connected to the heating element and the electrodes of the electroluminescent night light.

* * * * *

UNITED STATES PATENT AND TRADEMARK OFFICE
CERTIFICATE OF CORRECTION

PATENT NO.   : 6,302,559 B1
DATED        : October 16, 2001
INVENTOR(S)  : William D. Warren Page 1 of 1

It is certified that error appears in the above-identified patent and that said Letters Patent is hereby corrected as shown below:

<u>Column 3,</u>
Line 52, delete "enersization" and insert therefor -- energization --; and <u>Column 4,</u>
Line 2, delete "a n" and insert therefor -- an --.

Signed and Sealed this

Seventh Day of May, 2002

*Attest:*

*Attesting Officer*

JAMES E. ROGAN
*Director of the United States Patent and Trademark Office*